(12) United States Patent
Rillema

(10) Patent No.: US 6,238,644 B1
(45) Date of Patent: May 29, 2001

(54) METHOD FOR TREATING AND/OR IMAGING BREAST CANCER USING RADIOACTIVE IODIDE

(75) Inventor: James A. Rillema, Bloomfield Hills, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 09/145,515

(22) Filed: Sep. 2, 1998

Related U.S. Application Data

(60) Provisional application No. 60/056,315, filed on Sep. 3, 1997.

(51) Int. Cl.$^7$ ............................. A61K 51/00; A61M 36/14
(52) U.S. Cl. ........................ 424/1.61; 424/1.65; 424/1.85
(58) Field of Search ................................. 424/1.11, 1.65, 424/1.61, 1.81, 1.85, 9.1

(56) References Cited

U.S. PATENT DOCUMENTS

| | | | |
|---|---|---|---|
| 3,380,888 | * 4/1968 | Numerof et al. | 167/84.5 |
| 4,816,255 | 3/1989 | Ghent et al. | 424/150 |
| 5,011,677 | 4/1991 | Day et al. | 424/1.1 |
| 5,030,195 | 7/1991 | Nardi | 600/7 |
| 5,077,034 | 12/1991 | Kassis et al. | 424/1.1 |
| 5,096,694 | 3/1992 | Quivy et al. | 424/1.1 |
| 5,171,582 | 12/1992 | Ghent et al. | 424/667 |
| 5,185,142 | 2/1993 | Larson et al. | 424/1.1 |
| 5,250,304 | 10/1993 | Ghent et al. | 424/667 |
| 5,302,369 | 4/1994 | Day et al. | 424/1.29 |
| 5,308,604 | 5/1994 | Sinn et al. | 424/1.53 |
| 5,389,385 | 2/1995 | Ghent et al. | 424/667 |
| 5,589,198 | 12/1996 | Eskin et al. | 424/667 |

OTHER PUBLICATIONS

Henrich et al, European Journal of Nuclear Medicine, vol. 20, No. 3, pp. 225–230, Beta–oxidation of 1–[$^{14}$C]–17–[$^{131}$I]–iodohepta–decanoic acid following intracoronary injection in humans results in similar release of both tracers, Mar. 1993.*

Smyth, Annals of Medicine, vol. 29, No. 3, pp. 189–191, 'The Thyroid and Breast Cancer: A Significant Association', Jun. 1997.*

Bakir MA et al. "c–erbB2 protein overexpression in breast cancer as a target for PET using iodine–124–labeled monoclonal antibodies." J. Nucl. Med., Dec. 1992; 33 (12):2154–60 (abstract).

Percivale P et al. "Radioimmunoguided surgery after primary treatment of locally advanced breast cancer." J. Clin. Oncol., May 1996; 14(5): 1599–603 (abstract).

DeNardo SJ et al. "Radioimmunotherapy for breast cancer: treatment of a patient with I–131 L6 chimeric monoclonal antibody." Int. J. Biol. Markers, Oct.–Dec. 1991; 6(4):221–30 (abstract).

Peyrat J–P et al. "Characterization of prolactin receptors in human breast cancer." Breast Cancer Research and Treatment, 1984; 4,275–281.

Goldman MB et al. "Radioactive iodine therapy and breast cancer. A follow–up study of hyperthyroid women." Am. J. Epidemiol., May 1998; 127 (5):969–80 (abstract).

Bernard DJ et al. "Antagonism of prolactin binding by cyclosporine A on MCF7 breast tumour cell line." Anticancer Research, Nov.–Dec. 1991; 11(6):2147–51 (abstract).

Eskin BA et al. "Different tissue responses for iodine and iodide in rat thyroid and mammary glands." Biological Trace Element Research, Jul. 1995; 49(1):9–19 (abstract).

Eskin BA. "Iodine and mammary cancer." Adv. Exp. Med. Biol., 1977; 91: 293–304 (abstract).

DeNardo DA et al. "Prediction of Radiation Doses from Therapy Using Tracer Studies with Iodine–131–Labeled Antibodies." J. Nucl. Med., Dec. 1996. 37(12): 1970–1975.

Mester J et al. "Modulatin of [5–125I]Iododeoxyuridine Incorporation into Tumour and Normal Tissue DNA by Methotrexate and Thymidylate Synthase Inhibitors." Eur. J. Cancer, 1996. 32A(9): 1603–1608.

Hoffman DA et al. "Breast Cancer Following Iodine–131 Therapy for Hyperthyroidism." JNCI, Jan. 1983. 70(1):63–67.

Robbins, R. et al. "Localization of Immunoreactive Na–/I–Symporter (ir–NIS) in Normal and Neoplastic Human Thyroid Cells." abstract.

McGhee ED et al. "Regulation of the Sodium–Dependent Iodide Symporter in FRTL–5 Cells." Abstract.

* cited by examiner

*Primary Examiner*—Dameron Jones
(74) *Attorney, Agent, or Firm*—Gifford, Krass, Groh, Sprinkle, Anderson & Citkowski, P.C.

(57) ABSTRACT

The instant invention utilizes the preferential uptake of iodine by mammary cells in general, and neoplastic mammary cells in particular to promote the concentration of radioactive iodine in malignant mammary cells. Radioactive iodine has utility in the instant invention as both a cancer therapeutic and a radioimaging dye. Iodine 125 and/or iodine 131 are administered in doses from 1 to 50 milliCurie per day. Subsequent doses may also be administered as clinically warranted. Administration of hormones prior to, or simultaneous with, the administration of the radio iodine is optionally utilized to stimulate iodine uptake in neoplastic mammary cells or to inhibit iodine uptake by the thyroid gland.

21 Claims, No Drawings

METHOD FOR TREATING AND/OR IMAGING BREAST CANCER USING RADIOACTIVE IODIDE

RELATED APPLICATION

This patent application claims priority of provisional patent application 60/056,315, filed Sep. 3, 1997, entitled "Method for Treating and/or Imaging Breast Cancer Using Radioactive Iodide."

BACKGROUND OF THE INVENTION

It has long been known that iodide appears in the milk of mammals. The levels of iodide in the milk of a variety of mammals including humans are 20–30 fold higher than that present in the maternal plasma. Since about 50% of the iodide in milk is incorporated into milk proteins, the mechanisms that drive the accumulation of iodide in milk could include the functioning of an iodide transporter and/or enzymes involved in iodide incorporation into proteins. Early experiments showed a decreased $^{131}$I accumulation in milk when lactating rats were injected with perchlorate (an inhibitor of the iodide transporter) or methimazole (an inhibitor of peroxidase). Perchlorate was more potent in inhibiting total $^{131}$I uptake, whereas methimazole, primarily inhibited $^{131}$I binding to milk proteins. These in vivo studies suggest that both an iodide transporter and a peroxidase enzyme are present in mammary cells, and are involved in the accumulation of iodide in milk during lactation.

Studies in the literature focusing on the hormonal regulation of iodide transport in the mammary gland are limited. It has been reported that thyroid stimulating hormone (TSH) or thyroxin injected into lactating rats had no effect on $^{131}$I secretion into milk. In addition, prolactin (PRL), growth hormone (GH), insulin or cortisol had no effect on iodide uptake into cultured mammary tissues taken from lactating rats.

Studies in the literature concerning iodide uptake in neoplastic mammary cells reported that radioactive iodide concentration in biopsied human breast tissue with carcinoma or dysplasia is higher than in histologically normal tissues from the same patients.

SUMMARY OF THE INVENTION

The instant invention involves a method for treating a breast cancer of a patient. The method includes the administration of a radioisotope of iodine to the breast cancer of the patient in a dosage of between 5 and 50 milliCuries over the course of one day. Additional doses of iodine radioisotopes may be administered in dosage of between 1 milliCurie and 50 milliCurie as clinically warranted.

The instant invention utilizes a composition for mammary tissue uptake. This composition includes an inorganic radioactive iodide salt and a parenterally injectable carrier therefor. The radioactive iodide salt includes alkali metal iodides, alkali earth iodides, transition metal iodides, iodine pentoxide and iodine tribromide. Adjuvants are optionally added to this composition in order to increase iodine uptake by mammary tissue, and/or inhibit iodine uptake by the thyroid gland. The compositions of the instant invention find utility as breast cancer therapeutics and as radioimaging dyes.

DETAILED DESCRIPTION OF THE INVENTION

The treatment of breast cancer currently is limited to malignant growths large enough to be targeted surgically or by external radiation sources. In contrast, the instant invention delivers radioisotopes of iodine to mammary cells as an ion. Due to the selective uptake of iodide by mammary cells, malignant cell clusters too small to be otherwise treated receive a radiation dose. The treatment of breast cancer as described in the instant invention is effective in lessening the likelihood of metastasis and in inhibiting or killing cancerous cells.

The instant invention harnesses the natural ability of mammary cells to concentrate iodide internally. While the mechanisms of iodide uptake are not fally understood, a radioisotope of iodine is administered in vivo and generates therapeutic dosimetries of radioactive decay products in those tissues in which the cells concentrate iodide. A therapeutic administration ranges from between 1 milliCurie (mCi) and 50 milliCuries.

In order to further localize radioactive iodine uptake within mammary cells, substances are optionally administered which function to: 1) stimulate mammary cell uptake, such as prolactin or dopamine antagonists; or 2) inhibit uptake by other body tissues, such as thyroid hormones.

Substances are administered to further localize iodine uptake in mammary cells at times prior to, in concert with, or after the administration of the radioactive iodine, depending on the factors including pharmokinetics of the specific substance, the radiation dosimetry and the radioisotope half life.

The instant invention also finds application in the radioimaging of mammary tissues. Radiation flux variations which relate to cellular condition are detectable by conventional radioimaging techniques, owing to the increased metabolism of malignant cells relative to normal cells.

Based on the above observations, a method for treating breast cancer is described in the instant invention. While all radioisotopes of iodide are operative in the instant invention, it is preferred that $^{125}$I and/or $^{131}$I be administered to treat breast cancer, owing to the decay mode, decay energy, isotope half life and other properties. More preferably, $^{125}$I is administered to treat breast cancer.

The radioisotope of iodine is administered as an iodide salt that is soluble in a carrier solution compatible with physiological pH and molality. The radioisotope of iodine is administered in the form of an alkali metal, alkali earth or transition metal iodide, iodine pentoxide, or iodine tribromide compounds. Preferably, the radioisotope of iodine is administered as sodium iodide or potassium iodide.

The instant invention functions in part because an iodide transporter is present in neoplastic mammary cells. It is observed that radioactive iodide is concentrated by more than 80-fold in MCF-7 cells cultured for 10 minutes with $^{125}$I. MCF-7 cells are a neoplastic mammary cell line of human origin. These studies support the existence of an iodide transporter in at least certain neoplastic mammary cells.

The radioisotope of iodine is administered parenterally with a suitable carrier, for example in saline or buffered vehicles with or without various adjuvants. The adjuvants optionally include hormones to further increase the iodide transport in mammary cells and decrease the uptake of other cell types containing iodide transporters.

In a single bolus method of the instant invention, between 5 and 50 mCi of radioactive iodine is administered. Preferably, the iodine is administered as the sodium salt of $^{125}$I or $^{131}$I.

In a multiple bolus method of the instant invention between 1 and 50 mCi of radioactive iodine is administered per dosage. Between 2 and 20 such dosages are administered over a period of three days to four weeks. The individual dosages may be of equivalent dosimetry, or the dosimetry may vary between the doses. Preferably, the iodine is administered as the sodium salt of $^{125}$I or $^{131}$I.

In an infusion method of the instant invention, the radioisotope of iodine is administered intravenously by means of an infusion pump for from 1 day to 30 days. The daily dosimetry being between 1 and 50 mCi per day. Preferably the iodine is administered as the sodium salt of $^{125}$I or $^{131}$I.

Optionally, steps are taken to elevate prolactin levels, in order to stimulate the iodide uptake process in neoplastic mammary cells. In such instances, prolactin is administered for from three to sixty days prior to the administration of the radioisotope of iodide therapy. Prolactin, for such purposes is administered in doses ranging from 0.01 to 5 milligrams per kilogram body weight per day. Alternatively, clinically significant doses of a dopamine antagonist are administered for three to sixty days prior to the radioisotope therapy. The dopamine antagonist thereby serves to elevate endogenous prolactin levels.

The inventor has discovered that PRL doubles the rate of iodide accumulation in cultured mammary tissues taken from 12–14 day pregnant mice. In time course studies of the instant invention, it is observed that there is an initial effect of PRL after 4 hr, whereas a maximum two- to threefold increase in iodide accumulation occurs after 24 hr. In dose-response studies, 1 ng/ml PRL elicited a significant response, whereas PRL concentrations >5 ng/ml stimulated maximum responses. Other lactogenic hormones, including human growth hormone (GH) and human placental lactogens, also stimulated iodide uptake, whereas nonlactogenic substances, including bovine GH, bovine serum albumin, and thyroid-stimulating hormone, are without effect. PRL has no effect on iodide uptake into fat cells. In further studies, PRL stimulates iodide incorporation into macromolecules in a 10% trichloroacetic acid-precipitable tissue fraction, as well as in a pH 4.6 isoelectric precipitate. The findings from these studies demonstrate that PRL is effective in a treatment regime to stimulate both the accumulation of free iodide in milk and iodide incorporation into milk proteins. Actinomycin-D and cycloheximide are observed to abolish the PRL stimulation of iodide uptake and its incorporation into protein. Perchlorate and thiocyanate, inhibitors of the iodide transporter, also abolish the PRL effects on iodide uptake and incorporation. Similarly, propylthiouracil and aminothiazole, inhibitors of peroxidase, abolish both effects of PRL. Finally, the extent of iodide uptake in mammary cells is suppressed by about 50% in sodium free medium.

In a course of administering the radioisotope to a patient, increased treatment efficiencies and minimization of spurious irradiation of the thyroid gland is optionally performed. The thyroid gland is protected during the radioactive iodide therapy by administering therapeutic doses of thyroid hormones. These hormones illustratively include levothyroxine. Such hormones delivered in quantities of from about one to ten micrograms per kilogram body weight per day, for five days to four weeks preceding the radio iodide therapy is typically sufficient to limit thyroid tissue uptake of the radioisotope.

In another embodiment of the instant invention, in situ images of breast cancer cells are obtained based on inorganic iodide accumulation in such cells. Such images are obtained illustratively in computed axial tomography (CAT), positron emission tomography (PET) and magnetic resonance imaging (MRI). Furthermore, conventionally histological and immunological methods that employ iodide binding to a transporter protein in breast cancer cells are also appreciated to be within the scope of the instant invention.

A better understanding of the instant invention and of its many advantages should be had by referring to the following specific examples, given by way of illustration.

EXAMPLE 1

Mammary Tumor Stimulation in Rats.

Forty Holtzman Sprague-Dawley female rats (50 days of age) are given the mammary carcinogen, 9,10-dimethyl-1, 2-benzanthracene (DMBA); 15 mg/rat in sesame oil) by oral lavage. Then, 15 days later each rat is bilaterally ovariectomized and given a subcutaneous SILASTIC™ implant filled with crystalline estradiol to stimulate daily prolactin surges (as per Caligaris et al. J. Endocranial 60:205–215, 1974), which induce iodide transporters in mammary tissue and enhanced mammary tumor induction. Each rat is examined twice weekly for the presence of mammary tumors beginning 30 days after DMBA treatment. When three or more tumors that are larger than 5 mm×5 mm in size are present in a rat, then that rat will be used for experimentation.

EXAMPLE 2

Treatment of Mammary Tumors in Rats.

The rats will be weighed and placed in a rat restrainer and injected with carrier-free $^{131}$I Na (100 μCi/kg) via the tail vein. The injected animals are euthanized by a lethal injection of sodium pentobarbital (120 mg/kg, i.p.) at 2, 15 or 30 min or 1, 2, 4, 8 or 16 hours (5 rats per time point) after radioiodine injection. At the time of euthanasia, mammary tumors and non-tumorous mammary tissue, thyroid, salivary glands, skeletal muscle, liver, adipose tissue, and blood are collected. The tissue is cut into 5–10 mg pieces, each of which is weighed. A sample of each tissue collected is counted in a gamma counter directly. A second sample of each is homogenized in 3 ml 10% trichloroacetic acid (TCA) and centrifuged. Radioactivity in the TCA-precipitable (primarily proteins) and soluble fractions will be determined. Additional tissue samples are employed to assess intracellular and extracellular spaces in the tissue samples by equilibration with radio labeled [$^3$H]OH and $^{14}$C-sucrose (J. A. Rillema and T. X. Yu, Amer. J. Physiol 34: E879–E882, 1996). Intracellular uptake of radioactive iodide and its incorporation into protein is then be calculated. The tissue to blood ratio is also determined.

EXAMPLE 3

Rat Mammary Tumor Uptake of Iodide Radioisotope.

An in vivo time-course of radio labeled iodide uptake and incorporation is obtained for mammary tumors and a variety of "control" tissues, some of which are known to possess iodide transporters. Radiolabeled iodide is observed to selectively accumulate in mammary tumor cells.

EXAMPLE 4

$^{131}$I treatment of Rat Mammary Cell Tumors.

Two groups of 20 Holtzman Sprague-Dawley female rats each are treated with DMBA at 50 days of age as in Example 1. Similarly, all rats are ovariectomized and treated with estrogen as above. When three or more mammary tumors appear, one group (the experimental) is treated with carrier free $^{131}$I Na (100 μCi/kg) via the tail vein while the other group (the controls) is treated with an equivalent amount of nonradioactive NaI. Mammary tumor size and location is identified at the time of iodide treatment and twice a week thereafter for 30 days; the incidence of new tumors is also monitored. To maintain elevated estradiol and prolactin levels, the estradiol implants are replaced at 30 days and the animal's tumor status followed for an additional 30 days. Since spontaneous regression of tumors is sometimes observed in DMBA-treated animals, the control group allows for an estimation of spontaneous regression in the absence of radioiodine therapy. Likewise, tumor size may regress when the estradiol implants become exhausted. This is be assessed by inserting a new capsule at 30 days. After accounting for these factors tumor regression and inhibition are noted for only the experimental group.

EXAMPLE 5

$^{125}$I Treatment of Rat Mammary Cell Tumors.

The procedure as described in Example 4 except that $^{125}$I will be administered instead of $^{131}$I. After accounting for experimental factors, tumor regression and inhibition are noted for only the experimental group.

EXAMPLE 6

The Effect of Chronic $^{125}$I Treatment on Mammary Tumor Growth in Rats.

The procedure as described in Example 4, except that the iodide treatment will be done using, subcutaneously implanted Alzet osmotic minipumps (7, 14 or 28 day capacities) filled with carrier-free $^{125}$I (70, 140 or 280 μCi/minipump respectively; 3 experimental groups) or non-radioactive NaI (28 day osmotic minipump, one control group) and connected to a catheter implanted in the jugular vein. Mammary tumor growth and location is monitored twice weekly for 30 days. As tumor regression occurs, the estradiol implants are replaced with implants and the tumor status followed for another 30 days. After accounting for experimental factors, tumor regression and inhibition are noted for only the experimental group.

Any publications mentioned in this specification are indicative of the levels of those skilled in the art to which the invention pertains. These publications are herein incorporated by reference to the same extent as if each individual publication was specifically and individually indicated to be incorporated by reference.

Various modifications of the instant invention in addition to those shown and described herein will be apparent to those skilled in the art of the above description. Such modifications are also intended to fall within the scope of the appended claims.

What is claimed is:

1. A method for treating a breast cancer of a patient comprising the step of:
    administering a radioisotope of iodide selected from the group consisting of $^{125}$I$^-$ and $^{131}$I$^-$ to the breast cancer of the patient in a dosage of between 5 milliCuries and 50 milliCuries in a period of one day.
2. The method of claim 1 further comprising:
    administering a successive bolus of said radioactive iodide to the breast cancer of the patient, said bolus being between 1 milliCurie and 50 milliCurie per day following said dosage.
3. The method of claim 2 further comprising the step of:
    administering additional boli of said radioactive iodide over a period of less than four weeks.
4. The method of claim 1 wherein administering said radioisotope of iodide is accomplished by means of an infusion pump.
5. The method of claim 1 wherein said radioactive iodide is in a form selected from the group consisting of: an alkali metal iodide, alkali earth iodide, and transition metal iodide.
6. The method of claim 1 wherein said radioactive iodide is a radioisotope selected from the group consisting of: $^{125}$I and $^{131}$I.
7. The method of claim 1 wherein said radioactive iodide is in a form selected from the group consisting of: Na $^{125}$I and K $^{125}$I.
8. The method of claim 1 further comprising the steps of:
    a) delivering therapeutic doses of a thyroid hormone prior to administering said radioisotope; and
    b) allowing sufficient time prior to administration of said radioisotope for thyroid uptake of said radioisotope to be diminished.
9. The method of claim 1 further comprising the step of:
    a) elevating patient levels of prolactin so as to enhance the uptake of said radioisotope by the breast cancer.
10. The method of claim 9 wherein elevating prolactin levels is accomplished by the administration of therapeutic doses of prolactin.
11. A method for treating a breast cancer of a patient comprising the step of:
    elevating patient levels of prolactin by the administration of therapeutic doses of dopamine antagonist so as to enhance the uptake of said radioisotope by the breast cancer; and
    administering a radioisotope of iodine to the breast cancer of the patient in a dosage of between 5 milliCuries and 50 milliCuries in a period of one day.
12. A composition for mammary tissue uptake comprising:
    an inorganic radioactive iodide salt in contact with mammary tissue; and
    a carrier for said salt, said carrier suitable for parenteral injection.
13. The composition of claim 12 wherein said salt comprises a radioisotope of iodide selected from a group consisting of: $^{125}$I and $^{131}$I.
14. The composition of claim 13 wherein said radioisotope is present from between 1 and 50 milliCuries.
15. The composition of claim 13 wherein said salt is selected from a group consisting of: sodium iodide and potassium iodide.
16. The composition of claim 12 further comprising an adjuvant.
17. The composition of claim 16 wherein said adjuvant is selected from a group consisting of: prolactin, levothyroxine, a dopamine antagonist, human growth hormone and human placental lactogens.
18. A method for in situ imaging of breast cancer cells comprising the steps of:
    administering a composition of claim 12 to a breast cancer patient;
    allowing sufficient time for said composition to collect in mammary tissue of the breast cancer patient; and
    spatially imaging iodide within the mammary tissue of the breast cancer patient.

19. A method for treating a breast cancer of a patient comprising the step of:

administering between 1 and 50 milliCuries of $^{125}$I as a salt selected from a group consisting of: sodium iodide and potassium iodide to the breast cancer of the patient.

20. The method of claim 19 further comprising the step of: delivering a therapeutic dose of a compound to promote selective uptake of said salt by mammary tissue, said compound being selected from the group consisting of: prolactin, levothyroxine, a dopamine antagonist, human growth hormone and human placental lactogens.

21. A method of treating breast cancer of a patient comprising:

delivering therapeutic doses of levothroxine prior to administering a radioisotope of iodide to the breast cancer of the patient;

allowing sufficient time prior to administration of said radioisotope for thyroid uptake of said radioisotope to be diminished; and administering said radioisotope in a dosage of between 5 milliCuries and 50 milliCuries in a period of one day.

* * * * *